US006314320B1

(12) United States Patent
Powers et al.

(10) Patent No.: US 6,314,320 B1
(45) Date of Patent: Nov. 6, 2001

(54) METHOD AND APPARATUS FOR SELECTIVELY INACTIVATING AED FUNCTIONALITY

(76) Inventors: Daniel J Powers, 2145 Squak Mountain Loop SW., Issaquah, WA (US) 98027; Thomas D Lyster, 23309 21st Ave. SE., Bothell, WA (US) 98021; Karl A Woelfer, 1837 NE. Ravenna Blvd., Seattle, WA (US) 98105

( * ) Notice: Subject to any disclaimer, the term of this patent is extended or adjusted under 35 U.S.C. 154(b) by 0 days.

(21) Appl. No.: 09/411,347

(22) Filed: Oct. 1, 1999

(51) Int. Cl.[7] .................................................. A61N 1/39
(52) U.S. Cl. ........................................ 607/5; 607/4
(58) Field of Search .................................. 607/2, 4, 5, 7; 434/262, 265

(56) References Cited

U.S. PATENT DOCUMENTS

| | | | |
|---|---|---|---|
| 5,342,403 | * | 8/1994 | Powers et al. .......................... 607/5 |
| 5,391,187 | * | 2/1995 | Freeman ................................ 607/5 |
| 5,607,454 | * | 3/1997 | Cameron et al. ....................... 607/5 |
| 5,735,879 | | 4/1998 | Gliner et al. . |
| 5,800,460 | | 9/1998 | Powers et al. . |
| 6,021,349 | * | 2/2000 | Arand et al. ........................... 607/5 |

FOREIGN PATENT DOCUMENTS

WO 94/27674   12/1994  (WO) .

* cited by examiner

Primary Examiner—Jeffrey R. Jastrzab
Assistant Examiner—Frances Oropeza

(57) ABSTRACT

A novel apparatus for inactivating the AED prompting feature without inactivating the monitoring and analysis capability of the AED. AEDs are designed to be deployed by lay responders, such as flight attendants and police officers. As a result, in addition to a shock advisory algorithm which determines when a victim has a shockable rhythm, the devices also typically provide detailed prompts to the user. However, once a more advanced user arrives at the emergency (such as a paramedic) the detailed prompts are typically no longer required. The ability to silence the prompting feature without disabling the monitoring and analysis capability, as opposed to attaching the patient to another defibrillator, enables an advanced user to continue using the device.

19 Claims, 4 Drawing Sheets

METHOD AND APPARATUS FOR SELECTIVELY INACTIVATING AED FUNCTIONALITY

FIELD OF THE INVENTION

The present invention relates in general to defibrillators, particularly automatic or semi-automatic external defibrillators ("AED"). In particularly, this invention relates to a method of inactivating the AED functionality. Functionality may be selectively inactivated such that the monitoring and analysis capability is not inactivated. This invention relates to a single device capable of driving a patient care delivery protocol when operated by an inexperienced first tier responder, as well as having a user drive the patient care delivery protocol when operated by a trained second tier responder.

BACKGROUND OF THE INVENTION

Sudden cardiac death is the leading cause of death in the United States, with one person dying every two minutes and 70% of those deaths occurring in the home. Most sudden cardiac death is caused by ventricular fibrillation ("VF"), in which the heart's muscle fibers contract without coordination, thereby interrupting normal blood flow to the body. The only known effective treatment for VF is electrical defibrillation, in which an electrical pulse is applied to the patient's heart. The electrical pulse must be delivered within a short time after onset of VF in order for the patient to have any reasonable chance of survival. Electrical defibrillation may also be used to treat shockable ventricular tachycardia ("VT"). Accordingly, defibrillation is the appropriate therapy for any shockable cardiac rhythm, i.e., VF or shockable VT.

One way of providing electrical defibrillation uses an external defibrillator. External defibrillators send electrical pulses to the patient's heart through electrodes applied to the patient's torso. External defibrillators are typically located and used in hospital emergency rooms, operating rooms, and emergency medical vehicles. Of the wide variety of external defibrillators currently available, automatic and semi-automatic external defibrillators (referred to collectively as "AEDs") are becoming increasingly popular because they can be used by relatively inexperienced personnel. Such AEDs are also especially lightweight, compact, and portable. AEDs are described in U.S. Pat. No. 5,607,454 to Cameron et al. entitled "Electrotherapy Method and Apparatus" and PCT Publication No. WO 94/27674 entitled "Defibrillator with Self-Test Features", the specifications of which are incorporated herein.

AEDs provide a number of advantages, including the availability of external defibrillation at locations where external defibrillation is likely to be performed quite infrequently, such as in residences, public buildings, businesses, personal vehicles, public transportation vehicles, etc. AEDs contain an algorithm that enables the device to determine whether the victim has a shockable rhythm. Thus, the AED obviates the need for a trained user to interpret the ECG. Further, AEDs prompt the user in the correct protocol for administering care. For first tier responder (such as flight attendants and security guards), a device that delivers prompts with specific instructions is most effective. In this use model, because of the detailed prompting, the AED drives the patient care protocol.

One example of prompting provided by an AED is delivered by ForeRunner® by Heartstream. When a user turns the device on, the device prompts the user to "APPLY PADS." Once the electrode pads have been attached, the device will indicate to the user "ANALYZING HEART RHYTHM—DO NOT TOUCH THE PATIENT." Once the device determines that a shockable heart rhythm is present the device then prompt the user to "DELIVER SHOCK NOW—PRESS THE ORANGE BUTTON." After delivering the shock, the device then prompts "SHOCK DELIVERED—IT IS SAFE TO TOUCH THE PATIENT, CHECK AIRWAY, CHECK BREATHING, CHECK PULSE, IF NEEDED, BEGIN CPR." Other prompts may be delivered as well, depending on the set-up of the device and the condition of the patient.

One drawback to using an AED is that the prompts are designed for a lay responder and there is no way to alter or disable the prompts during use in an emergency without changing the underlying operation of the AED. Thus when a more advanced caregiver arrives at the scene of an emergency (such as an EMT or paramedic), he or she may not wish to disconnect the victim from the AED and attach a paramedic defibrillator (which may also include the ECG analysis but only features limited prompts) since there is a possibility that the victim will revert into sudden cardiac arrest during the time that the AED is removed and prior to the time another device is attached. Additionally there would be a discontinuity to any ECG data that was collected for the victim since the initial data would be recorded by the first responder AED and subsequent data would be recorded by the paramedic defibrillator. However, second tier responders typically have additional training and are more likely to drive the patient care protocol. As a result, the advanced caregiver will not need or want to be given the detailed prompting by the AED. However, the only way to disable the prompts in an AED is to turn the device off. Thus, if the device is left on, the advanced caregiver will be forced to listen to unnecessary and often distracting prompts.

Thus, when emergency response personnel are called to the scene of a cardiac arrest or a patient is transferred to the emergency room, the ability to inactivate the prompting feature of an AED is desirable. Further, it is desirable to inactivate the prompting features of an AED without inactivating the monitoring and analysis functionality of the AED.

Thus, it is an object of the present invention to provide medical personnel with an AED that allows the user to inactivate the prompting functionality of the device without inactivating the analysis algorithm.

SUMMARY OF THE INVENTION

A method of treating a patient with an AED comprising: monitoring patient ECG data; analyzing patient ECG data for the presence of a shockable rhythm; prompting a rescuer based on an analysis of the monitored patient ECG data; and quieting the prompting step upon activation of user input. The monitoring and analyzing steps may still be performed during the quieting step. Further the method may include the step of discontinuing the analyzing step in response to the quieting step. In one embodiment, the quieting step is activated by user intervention. Specifically, the quieting step may be activated by an advanced caregiver. Ideally, the monitoring step occurs automatically without user intervention. Additionally, the analyzing step occurs automatically without user intervention. More specifically, the analyzing step occurs upon activation of user input. When the AED is used as a trainer, the patient ECG data is retrieved from memory. After inactivation of the prompting feature, the prompting feature may be reactivated by inactivating the quieting step. This is accomplished by user intervention. Or in response to a timer.

An AED comprising: a controller, an energy delivery system operable by the controller to deliver an electrical shock from an energy source to an electrode interface, a monitor for collecting patient ECG data; an analyzer for analyzing the patient ECG data; a user instruction output operable by the controller to prompt a user based on information received the analyzer; and a user input for selectively inactivating the user instruction output. In one embodiment, the AED continues to collect patient ECG data and the analyzer continues to analyze the patient ECG data after inactivation of the user instruction output. The user instruction output of the AED may include a visual image generator. Additionally, the user instruction output may include an audible sound generator. User input may be accomplished via a soft key. In one embodiment, even upon inactivation of user prompts, the AED will deliver a user prompt in response to a shockable cardiac rhythm.

A defibrillator capable of dynamic patient care protocol delivery wherein: if a pause mode has been activated then the defibrillator enables the user to drive the patient care protocol; or if a pause mode has not been activated then the defibrillator drives the patient care protocol for the user.

DETAILED DESCRIPTION OF THE INVENTION

The following discussion is presented to enable a person skilled in the art to make and use the invention. Various modifications to the preferred embodiment will be readily apparent to those skilled in the art, and the generic principles defined herein may be applied to other embodiments and applications without departing from the spirit and scope of the present invention as defined by the appended claims. Thus, the present invention is not intended to be limited to the embodiment shown, but is to be accorded the widest scope consistent with the principles and features disclosed herein.

Figure 1:
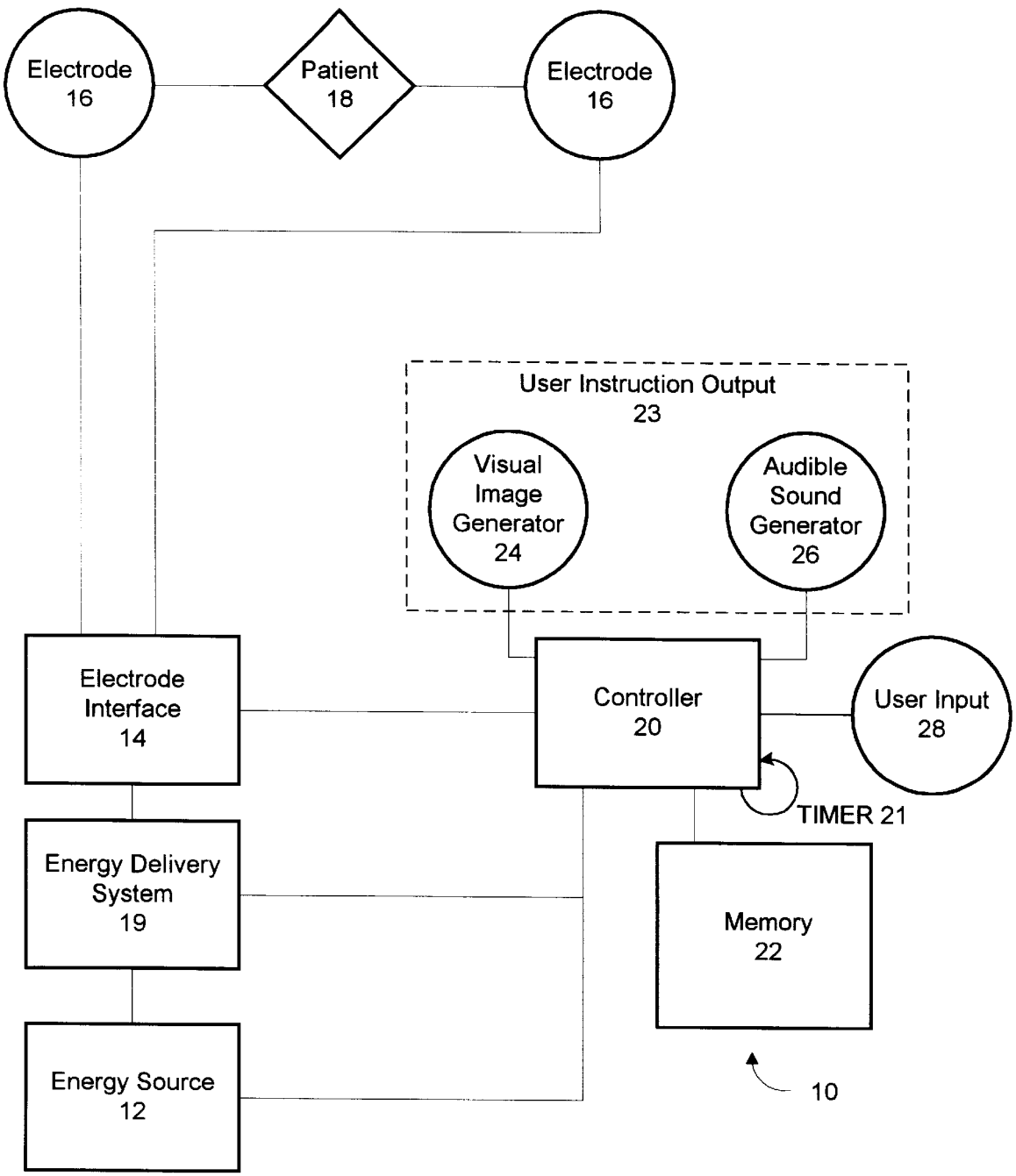
FIG. 1 is a block diagram of an AED suitable to employ the methods of the present invention.

FIG. 1 is a schematic block diagram of a defibrillator system 10 according to a preferred embodiment of this invention. The defibrillator system 10 comprises an energy source 12 to provide voltage or current pulses. A controller 20 operates an energy delivery system 19 to selectively connect and disconnect energy source 12 to and from a pair of electrodes 16 electrically attached to a patient 18 through an electrode interface 14 to provide electrotherapy to the patient. The defibrillator system 10 is an electrotherapy device such as an AED. Alternatively, defibrillator system 10 may be a defibrillator trainer that simulates the behavior of an AED in use, in which case the electrode interface and energy delivery system may be omitted. Controller 20 also includes a timer 21. Timer 21 may be used, for example, to terminate a pause or quiet mode.

Memory 22 records data collected by the AED while monitoring and treating a patient. Memory 22 may include any appropriate memory device such as FLASH, EEPROM, ROM or RAM. Memory 22 may be removable or, alternatively, may be integral with the AED.

An automated user instruction output 23 is provided which consists of a visual image generator 24 and an audible sound generator 26. Visual image generator 24 may display, among other things, instructions to the user for AED operation as well as patient ECG data. The visual image generator 24 may be, for example, a liquid crystal display ("LCD"). Additionally, an audible sound generator 26 may be provided that instructs the AED user in use of the AED. Activation of the visual image generator 24 and the audible sound generator 26 is controlled by the controller 20 in response to the information received from memory 22.

Additionally, user input 28 may be provided to interact with the memory 22 to enable a user to pause or inactivate the AED instruction functionality. Currently available override features in an AED include manual override for delivering a shock. For example, the Heartstream ForeRunner enables an advanced user to override the shock advisory algorithm decision that no shock is necessary by allowing the advanced user to deliver a shock.

Currently available AED operating modes include patient treatment (in which, e.g., a therapeutic pulse is delivered to a patient via energy delivery system 19), monitoring (in which, e.g., the patient's ECG is monitored), and self-test mode (in which defibrillator system 10 runs self-test procedures to determine its operating condition).

In addition to currently available operating modes, the AED of this invention includes a quiescent or pause mode (in which the defibrillator system 10 prompting is suspended). In any of its operating modes, defibrillator system 10 can communicate event data with memory 22.

During operation in patient treatment mode, defibrillator system 10 may collect event information relating to the patient (such as patient ECG) and event information relating to the device itself (such as the charging of energy delivery and monitoring module in preparation for a shock or the delivery of the shock itself). Controller 20 transmits this event information to memory 22. In addition, controller 20 may associate time information taken from a clock (not shown) with the event data and stores the associated time information in memory 22 as well.

During operation in quiescent mode, defibrillator system 10 pauses the prompting functionality. In one embodiment, the system may pause all prompting functionality. Alternatively, the system may selectively pause prompting functionality. In that situation, for example, all prompting would be paused, except the prompt "SHOCK ADVISED" or alternatively "CHECK PATIENT" (thus alerting the caregiver that a shockable rhythm had been detected). In one embodiment, selective prompting is available where monitoring and analysis of patient ECG continues to occur.

The defibrillator system 10 may concurrently either continue to monitor the patient condition in the background or may discontinue patient monitoring as well. Quiescent mode may be activated either by a dedicated user actuation button, or by the use of soft keys. Quiescent mode may be discontinued at any time, thus allowing the AED to return to automated prompting mode which includes delivery of user prompts. Subsequent termination of the quiescent mode can either be accomplished by a dedicated actuation button, by the use of soft keys, or by expiration of a timer (for example, where a timer has been pre-fixed to end the quiescent mode after a predetermined period of time). It will be appreciated by those of skill in the art that even where a dedicated activation button is provided, soft keys may be used subsequently to end the quiescent mode.

Figure 2:
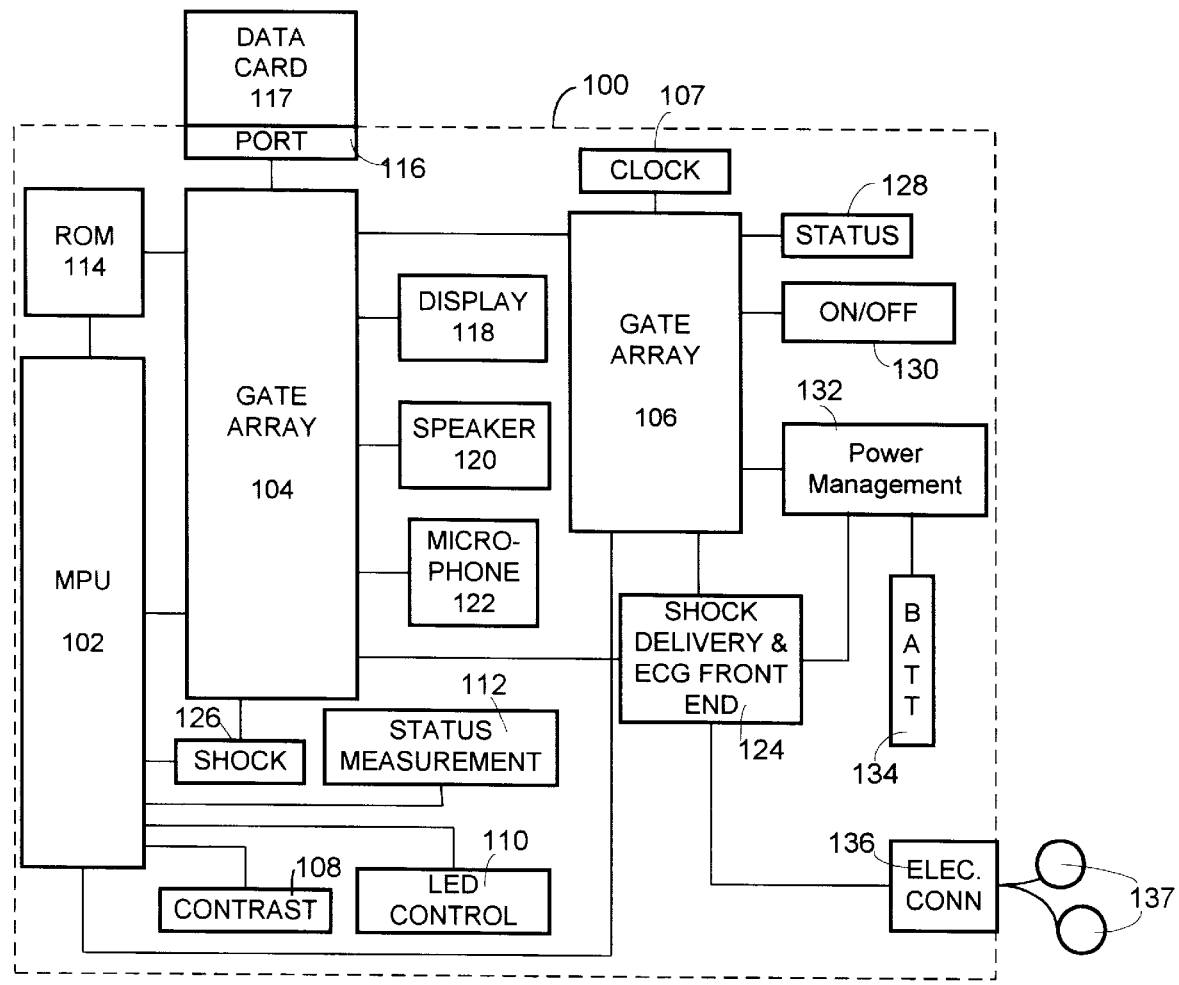
FIG. 2 is a block diagram of an AED of the invention.

The major components of an AED 100 according to a preferred embodiment are shown in FIG. 2 in block diagram form. AED 100 control functions are divided among a microprocessor unit (MPU) 102 and two custom gate arrays 104 and 106. It should be understood, however, that gate arrays 104 and 106 are optional, and their functions can be performed by other circuits.

MPU 102 performs program steps according to software instructions provided to it from ROM 114. MPU 102 controls the operation of certain buttons (such as display contrast buttons 108) and certain system LED's 110 (such as LED's associated with the shock button and the electrode connector). MPU 102 also receives system status information as shown by block 112. MPU 102 also controls the operation of the display contrast button 108 which may also function as soft keys, such as when the device is in quiet mode.

Gate array 104 implements the memory map to system ROM 114, data card port 116 and other system memory elements. System ROM 114 is preferably flash ROM, although EPROM or any other electrically erasable and programmable nonvolatile memory could be used. Where a data card port 116 is provided as a means to enable patient data to be removed from the AED 100, it is preferable that a data card slot configured to interface with PC data cards conforming to the 1995 PC Card standard be provided.

Gate array 106 provides a system monitor function by performing automatic self-tests of the defibrillator and its components. The gate array 106 displays the operational status of the defibrillator on a status display 128. Gate array 106 is also the defibrillator's interface with a user-activated on/off switch 130.

Gate array 106 controls the power management subsystem 132 to provide power to operate system components from battery 134 and to provide energy to the shock delivery system's capacitor(s) for a therapeutic shock during treatment mode. Power management subsystem 132 enables energy from the battery 134 to be delivered to the patient 18 via shock delivery and ECG front end 124. For that purpose, power management subsystem 132 includes a capacitor (not shown). Gate array 106 also interfaces with the defibrillator's ECG front end 124, enables the shock delivery system to deliver a shock in response to detection of a patient ECG pattern requiring treatment (and actuation of the shock button), and controls delivery of the shock to electrode connector 136 in response to shock delivery status information obtained during delivery of the shock. Further information regarding this last function may be found in U.S. Pat. No. 5,735,879 for "Electrotherapy Method for External Defibrillators" and U.S. Pat. No. 5,607,454 for "Electrotherapy Method and Apparatus," the disclosures of which are incorporated herein by reference.

As discussed above, the AED 100 can be operated in different modes, such as self-test mode, stand-by mode and patient treatment mode. Further discussion of the operation of an external defibrillator in self-test mode, stand by mode and patient treatment mode is provided in U.S. Pat. No. 5,800,460, the specification of which is incorporated herein.

During patient treatment mode, the AED receives ECG information from a patient through electrodes 137. The AED then analyzes the ECG information to determine whether a therapeutic shock is advised, and delivers a shock to the patient through the electrodes if a shock is advised and if the shock button 126 is actuated by a user. Typically, the AED communicates with the user in response to the monitored signal. For example, if artifact is detected, the AED will instruct the user not to touch the patient. If a shockable rhythm is detected, the AED will begin charging a capacitor in preparation for delivery of a shock and will instruct the user that a shock is advised.

During the quiescent mode provided according to this invention, the shock delivery and ECG front end 124 may continue to monitor the patient's condition as before. Where the ECG front end 124 continues to monitor the patient's condition, MPU 102, upon receiving information from the ECG front end 124, would NOT communicate with gate array 104 to deliver instructions to the user via display 118 or speaker 120 in response to each detected condition. More specifically, for example, AED would not automatically instruct the user not to touch the patient in response to the presence of artifact. Thus, the AED prompt function is inactivated resulting in a suspension of the automatic protocol (or an "auto protocol suspend" mode). However, if the prompting is only selectively suspended, then the AED would only instruct the user, for example, in response to the presence of a shockable rhythm (for example, advising the user "SHOCK ADVISED" or "CHECK PATIENT").

Where the prompt function is suspended and the analysis is suspended, the ECG front end 124 no longer monitors the patient's condition. Thus, ECG front end 124 would not communicate with gate array 104.

Figure 3:
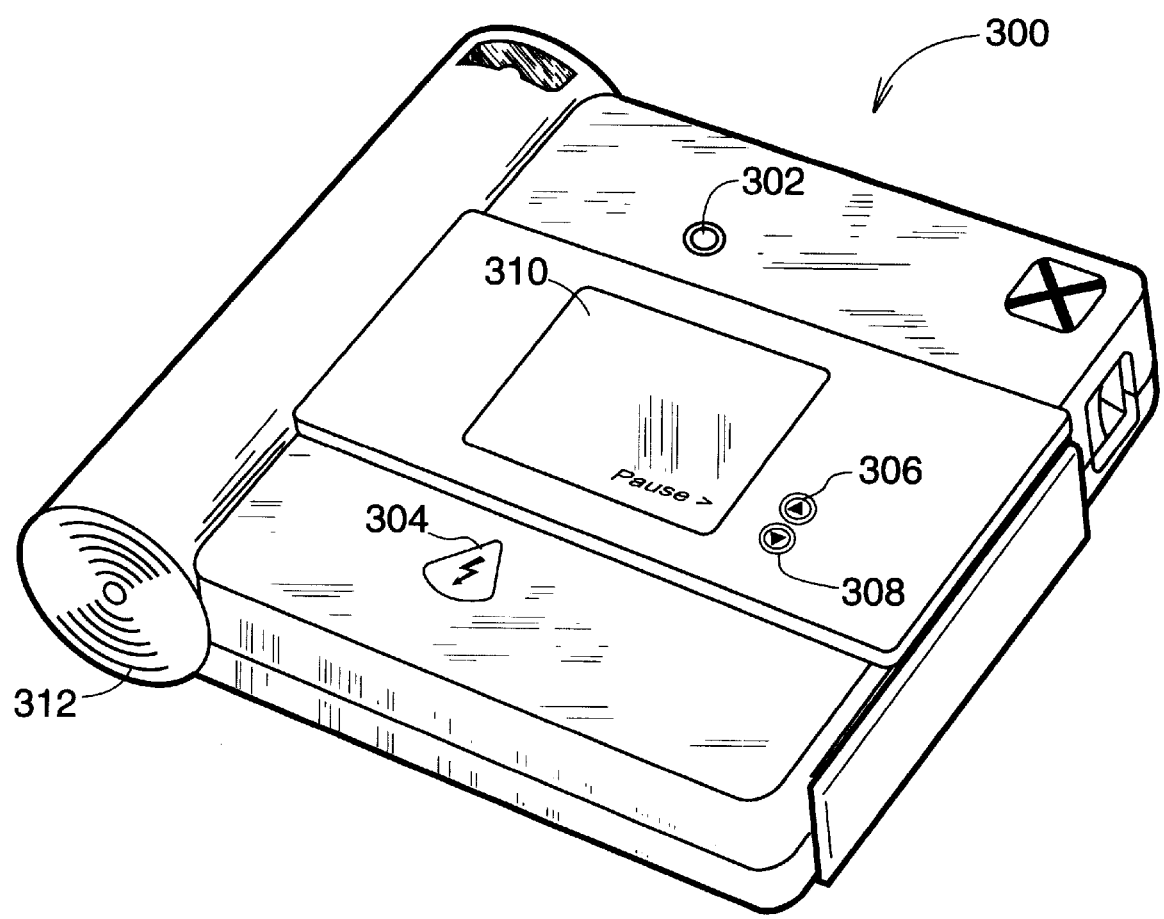
FIG. 3 is a top elevational view of an AED with an override function.

In a preferred embodiment, the invention is incorporated into the Heartstream FORERUNNER® AED. As shown in FIG. 3, the FORERUNNER AED 300 has four user inputs: an on/off or power button 302; a shock button 304; and two display contrast buttons 306 and 308. An LCD 310 provides text and/or graphic display and a speaker 312 provides audio output. In operation, the display 310 contrast button 308 as a soft key to select "PAUSE." "Pause" would then be visible on the display 310

Figure 4:
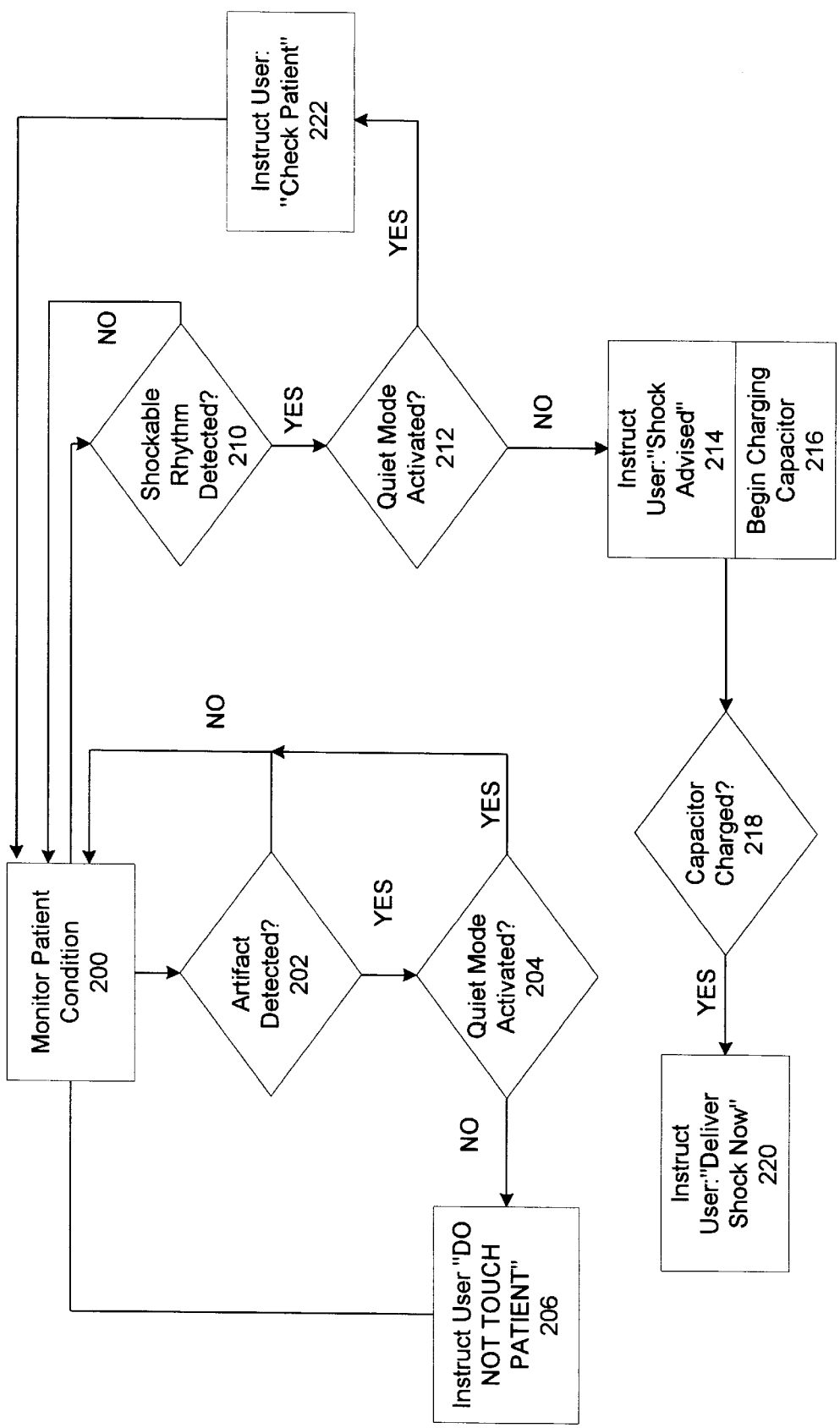
FIG. 4 is a flow chart demonstrating an operation of an AED capable of replaying event data.

FIG. 4 is a flow chart showing an operation of the shock delivery and ECG front end 124 as controlled by the MPU 102 during an auto protocol suspend mode when the defibrillator continues to monitor the patient's condition.

As shown by block 200, the AED is in monitor/therapy mode. At this time, the shock delivery and ECG front end 124 are monitoring patient condition 200. If artifact is detected 202, then the MPU 102 determines whether quiescent mode has been activated 204. In this example, quiescent mode is represented as a full suspension of the prompting features. If quiescent mode has been activated, then no instruction is provided to the user. In this embodiment, the AED continues to monitor patient condition 200. Quiescent mode 204 remains active until a programmable time-out occurs or until the operator presses "resume."

As discussed above, full or partial suspension of the prompts may be selected depending on the defibrillator configuration. If full suspension has been selected, then the defibrillator will not advise the user in response to a shockable rhythm. However, if only partial suspension of the prompts has been selected, the defibrillator would operate as shown in FIG. 4. Thus, when the defibrillator detects a shockable rhythm 210, the MPU 102 again determines whether quiescent mode has been activated 212. If quiescent mode has not been activated, then MPU 102 activates the prompt sequence appropriate for detection of a shockable rhythm. The AED first instructs the user that a "Shock is Advised" 214 and then begins charging the capacitor in preparation for delivery of a shock 216. If the capacitor has been charged 218, then the AED instructs the user to "DELIVER SHOCK NOW" 220. If, however, the quiescent mode has been activated 212, then the user is instructed to "CHECK PATIENT" 222. Importantly, no additional steps are taken, other than continuing to monitor the patient.

As discussed above, if desired, the caregiver may exit the quiescent mode and resume the fully functional monitoring and treatment mode associated with AED operation by terminating the quiescent mode. Alternatively, the caregiver may end the therapy session for the AED altogether by turning the AED off.

As will be appreciated by those of skill in the art, the quiescent mode can be activated and terminated in a variety of ways. For example, dedicated buttons may be provided for that purpose, or soft keys may be provided.

It should be appreciated that the scope of the invention is not limited to the embodiments described above. Various modifications and alterations might be made by those of skill in the art without departing from the scope and spirit of the present invention.

What is claimed is:

1. A method of treating a patient with an AED comprising:
    monitoring patient ECG data;
    analyzing patient ECG data for the presence of a shockable rhythm;
    prompting a rescuer based on an analysis of the monitored patient ECG data; and
    at least partially quieting the prompting step while still performing at least the monitoring step upon activation of user input.

2. The method of claim 1 wherein the monitoring and analyzing steps are still performed during the quieting step.

3. The method of claim 1 wherein the quieting step is activated by user intervention.

4. The method of claim 1 wherein the quieting step is activated by an advanced caregiver.

5. The method of claim 1 wherein the monitoring step occurs automatically without user intervention.

6. The method of claim 1 wherein the analyzing step occurs automatically without user intervention.

7. The method of claim 1 wherein the analyzing step occurs upon activation of user input.

8. The method of claim 1 wherein the patient ECG data is retrieved from memory.

9. The method of claim 1 further comprising the step of reactivating the prompting step by inactivating the quieting step.

10. The method of claim 9 wherein the quieting step is terminated by user intervention.

11. The method of claim 9 wherein the quieting step is terminated is response to a timer.

12. The method of claim 1 wherein the prompting step is fully quieted.

13. An AED comprising:
    a controller,
    an energy delivery system operable by the controller to deliver an electrical shock from an energy source to an electrode interface,
    a monitor for collecting patient ECG data;
    an analyzer for analyzing the patient ECG data;
    a user instruction output operable by the controller to prompt a user based on information received the analyzer; and
    a user input for selectively at least partially inactivating the user instruction output while still performing at least the monitoring step.

14. The AED of claim 13 wherein the monitor continues to collect patient ECG data and the analyzer continues to analyze the patient ECG data after inactivation of the user instruction output.

15. The AED of claim 13 wherein the user instruction output includes a visual image generator.

16. The AED of claim 13 wherein the user instruction output includes an audible sound generator.

17. The AED of claim 13 wherein the user input is a soft key.

18. The AED of claim 13 wherein upon the selective inactivation of user instruction, the AED delivers a user prompt in response to a shockable cardiac rhythm.

19. The AED of claim 13 wherein the user instruction is fully inactivated.

* * * * *